United States Patent [19]

Urwin

[11] 4,012,338

[45] Mar. 15, 1977

[54] PROCESS FOR MANUFACTURING A CARRIER OF TITANIUM DIOXIDE

[75] Inventor: Donald Urwin, Cleveland, England

[73] Assignee: Tioxide Group Limited, Cleveland, England

[22] Filed: July 10, 1975

[21] Appl. No.: 594,872

[30] Foreign Application Priority Data

Aug. 10, 1974 United Kingdom ............ 35347/74

[52] U.S. Cl. .............................. 252/461; 423/610; 423/612
[51] Int. Cl.² ......................................... B01J 21/06
[58] Field of Search ........... 252/461; 423/610, 612, 423/615; 106/73.3

[56] References Cited

UNITED STATES PATENTS

| | | | |
|---|---|---|---|
| 2,285,485 | 6/1942 | Barksdale et al. ................ | 423/612 |
| 3,092,457 | 6/1963 | Sprague .......................... | 252/461 X |
| 3,215,644 | 11/1965 | Kakinoki et al. ............... | 252/461 X |
| 3,297,411 | 1/1967 | Dear ................................ | 423/612 |
| 3,565,919 | 2/1971 | Friedrichsen et al. ......... | 252/461 X |
| 3,898,321 | 8/1975 | Marsh ............................. | 252/461 X |
| 3,910,851 | 10/1975 | Messing ......................... | 252/461 X |

Primary Examiner—W. J. Shine
Attorney, Agent, or Firm—Schuyler, Birch, Swindler, McKie & Beckett

[57] ABSTRACT

A carrier for a catalyst which is composed of particulate titanium dioxide having a hardness of at least 40, a bulk density of at least 0.8 grams per milliliter and a specific area of less than 5 square meters per gram. The carrier is particularly useful for supporting enzymes or vanadium pentoxide.

11 Claims, No Drawings

PROCESS FOR MANUFACTURING A CARRIER OF TITANIUM DIOXIDE

This invention relates to products and particularly to titanium dioxide products and to methods for their manufacture.

According to the present invention a carrier for an active entity comprises particulate titanium dioxide having a hardness measured as hereinafter defined of at least 40, a bulk density of at least 0.8 grams per milliliter, and a specific surface area of less than 5 square metres per gram.

According to a preferred form of the invention a carrier for an active entity comprises particulate titanium dioxide having a hardness measured as hereinafter defined of at least 40, a bulk density of at least 0.8 grams per milliliter, a specific surface area of less than 5 square metres per gram and contains aluminium expressed as $Al_2O_3$ in an amount of 0 to 0.2% by weight, silicon expressed as $SiO_2$ in an amount of 0 to 0.02% by weight, phosphorus expressed as $P_2O_5$ in an amount of 0 to 0.8% by weight, sulphur expressed as $SO_3$ in an amount of 0 to 0.2% by weight, potassium expressed as $K_2O$ in an amount of 0 to 0.4% by weight and zinc expressed as ZnO in an amount of 0 to 2% by weight of the carrier and also calcium expressed as CaO in an amount of 0 to 200 parts per million, antimony expressed as $Sb_2O_3$ in an amount of 0 to 200 parts per million and sodium expressed as $Na_2O$ in an amount of 0 to 200 parts per million.

The present invention provides a carrier for an active entity. The active entity may be, for example, a biologically active entity such as an enzyme or may be an organic catalytic material or inorganic catalytic material or component. It has been found that the use of titanium dioxide according to the present invention as a support or carrier for these types of active entities is beneficial in securing adequate contact between the entity and the substrate as well as in certain uses providing improvements in the yield or conversion or efficiency of the reaction which is to be catalysed.

Basically the product of the present invention is titanium dioxide which has a hardness when measured as hereinafter defined of at least 40 and a bulk density of at least 0.8 grams per milliliter and a specific surface area of less than 5 square meters per gram. Preferably, the product has a specific surface area of less than 3 square meters per gram and most advantageously the product has a specific surface area of from 0.6 to 2 square meters per gram.

It is also preferred that the product should have a bulk density greater than 1.0 grams per milliliter and particularly advantageous materials have been found to have a bulk density of from 1.2 to 1.8 grams per milliliter.

When the product is to be used as a carrier for a biologically active entity such as an enzyme, then it has been found advantageous that the product of the present invention should preferably have a hardness of at least 65. Products having a hardness of 100 can be used although it has been found that products having a hardness of from 85 to 100 are entirely satisfactory when used for this purpose.

The titanium dioxide product may be in the anatase crystalline form or in the rutile form, although it is preferred that the titanium dioxide should contain at least 50% by weight in the rutile configuration. Preferably, the product contains at least 90% by weight of the titanium dioxide in the rutile configuration.

Titanium dioxide is obtained from an ore, invariably a titaniferous ore containing the titanium dioxide in combined form with iron. Various methods are known for the separation of titanium dioxide from the various ores available, but basically the processes employed are known as the "Sulphate process" and the "Chloride process."

In the "sulphate" process for the manufacture of titanium dioxide a titaniferous ore is digested at an elevated temperature with concentrated sulphuric acid to produce a cake which is subsequently dissolved in water. The solution of titanyl sulphate obtained mixed with the iron compound is then subjected to various well known operations prior to hydrolysis to precipitate a hydrated form of titanium dioxide. The iron impurities remain in the solution and are separated from the precipitated hydrated titanium dioxide. The hydrated titanium dioxide is then usually calcined at an elevated temperature, say 800° to 1300° C to produce particulate titanium dioxide. This product can be obtained in either the anatase or rutile form dependent on the particular manner of hydrolysis and on the presence or absence of various additives during calcination.

In the "chloride" process for the manufacture of titanium dioxide a titaniferous ore, such as mineral rutile, is chlorinated to produce titanium tetrachloride. This titanium tetrachloride is purified to separate therefrom iron chlorides and other chlorinated impurities and is then oxidised in the vapour stage to produce titanium dioxide. This reactor discharge is obtainable either in the anatase or the rutile form depending on the presence or absence of additives during the oxidation process.

The products of the present invention may be obtained by treating raw titanium dioxide, i.e. the calciner discharge or the reactor discharge by heating at an elevated temperature. For instance, an anatase titanium dioxide obtained either from the "sulphate" or the "chloride" process may be heated to a temperature of at least 850° C to produce a product containing a mixture of anatase titanium dioxide and rutile titanium dioxide in proportions governed by the temperature to which the titanium dioxide is heated. Heating the product to a temperature of 850° C has been found to produce a product having a substantial proportion of anatase whereas heating to a temperature of 1200° C has been found to produce a product containing a high percentage of rutile titanium dioxide. Preferably the product is heated at a temperature of at least 1050° C to produce a product containing at least 50% by weight of the titanium dioxide in the rutile form. Usually the product will be heated to a temperature not exceeding 1300° C.

The time of heat treatment of the anatase titanium dioxide also controls, to some extent, the actual form of the product obtained, but usually the titanium dioxide will be heated for a time of at least one hour. Extended heating at an elevated temperature is not advised since sintering of the particles can occur which is undesirable.

A particular method for the manufacture of the products of the invention is to use as the starting material, granular anatase titanium dioxide. This form of titanium dioxide usually has an average particle size range of less than 840 microns. This granular anatase is usually sieved to select therefrom a desired fraction e.g.

having the particle size range of from 150 microns to 350 microns or from 180 microns to 600 microns or any other desired range depending on the final method of uses of the catalyst. This fraction is then heated at the appropriate elevated temperature to obtain the product having the desired content of rutile titanium dioxide. It has been found that products having good qualities may also be obtained by subjecting the sieved fraction of the granular anatase to a pelletising process prior to heat treatment at the elevated temperature. For instance, the sieved fraction may be placed in a rotating drum and tumbled for a period of from 1 to 6 hours.

For a drum having an internal diameter of from 2 to 8 inches it has been found advantageous to rotate the drum at a speed of from 50 to 100 revolutions per minute to effect the pelletisation.

The rutile titanium dioxide obtained from the sulphate process or the chloride process can be treated in a manner similar to that described above for anatase titanium dioxide. However, it is usual to use the anatase form of titanium dioxide obtained from the two basic processes i.e. the "sulphate" or "chloride" processes, as the starting material for the production of the products of the present invention.

A further method for the manufacture of the products of the invention is to neutralise titanium tetrachloride. For instance, an aqueous solution of titanium tetrachloride is neutralised by adding thereto an alkali e.g. ammonium hydroxide solution. Usually, the titanium tetrachloride is boiled during the addition of the ammonium hydroxide solution and an amount of ammonium hydroxide solution is added such that the pH of the mixture is maintained alkaline, i.e. greater than pH 7. After the completed addition of the ammonium hydroxide solution the mixture may be heated for a further period prior to filtering off the precipitated titanium dioxide product. This product is then heated to a temperature usually above 850° C, say 900° C to 1000° C as described hereinbefore for the manufacture of the products of the invention.

Alternatively to adding ammonium hydroxide solution to an aqueous solution of titanium tetrachloride, the aqueous solution of titanium tetrachloride may be added to the ammonium hydroxide solution. In this case it is found that a gel of titanium dioxide precipitates immediately, but this redissolves if the pH of the reaction mixture falls below about pH 6. Usually in this method, after the addition of the aqueous titanium tetrachloride solution, a further addition of ammonium hydroxide solution is made to adjust the pH to about pH 8.

Heating of the titanium dioxide, whether it be a granular anatase titanium dioxide or precipitated titanium dioxide from the hydrolysis of titanium tetrachloride solution, has not only been found to increase the bulk density to the required level, but also to produce a product having the required hardness.

The carriers according to the present invention have been found particularly useful for acting as a support for an inorganic catalyst component. It has been found that the carriers are particularly used as a support for a catalyst based on a transitional metal oxide such as vanadium pentoxide which is known as a catalyst in the oxidation of certain aromatic hydrocarbons. Vanadium pentoxide catalysts are known in the oxidation of o-xylene to produce phthalic anhydride.

The catalysts may be prepared by forming a bed of the carrier according to the present invention maintained in a fluid suspension by passing an inert gas, or air or oxygen through the bed. The bed is heated to an elevated temperature of the order of 800° to 1100° C, say 900° C, and vanadium pentoxide powder is gradually added to the fluid bed to coat the particles of the carrier.

The catalysts may also be prepared by mixing the carrier according to the present invention and powdered vanadium pentoxide and subsequently heating the mixture at a temperature of say 900° to 1000° C in a quartz tube. After heating, the powder is found to have sintered and requires grinding after cooling and usually sieving prior to use as a catalyst.

A further alternative method of manufacture of a catalyst is to form the carrier particles into a heated packed bed in a tube and to allow molten vanadium pentoxide to drain through the tube to contact the carrier particles.

As stated previously herein, the carrier according to the present invention may be used to support a biologically active entity such as an enzyme. Typical enzymes are pullalanase, carboxypeptidase, dextranase or papain. Such treated enzymes, for example papain, carried on this titanium dioxide of the present invention, may be used to treat beer on a continuous basis for an extended period of time for the reduction of haze.

In accordance with the present invention the carrier comprises particulate titanium dioxide having a hardness of at least 40. The hardness is measured using the following equipment: Gallenkamp magnetic stirrer hot plate, standard 600 ml beaker 12.3 cm high and 9.6 cm diameter, magnetic stirrer-polyethylene coated having a length of 4.5 cm and a diameter of 0.7 cm and one Buchner funnel.

The procedure for the determination of the hardness is as follows: Add 300 ml of distilled water to the beaker. Place the magnetic stirrer in the beaker. Weigh to an accuracy of ±0.05 grams, 15.0 grams of the carrier to be tested. Commence stirring the distilled water at a speed such that a vortex forms within the water and then add the weighed carrier.

In carrying out the stirring, it is important that the stirrer rotates as quickly as possible, but there is a limit to this since at high speeds with certain carriers, the stirrer tends to lose contact with the bottom of the beaker and produces irregular stirring of the mixture. It has been found that the most appropriate speed for all carriers is 750 to 800 r.p.m.

The mixture is stirred for 30 minutes and the slurry so obtained is then allowed to settle for 5 minutes. The supernatant liquor is decanted carefully and to the beaker is then added 300 mls of distilled water. The slurry is allowed to settle for 5 minutes and the supernatant liquor is decanted carefully again.

The residue remaining in the beaker is filtered using a Buchner funnel, washed with acetone and dried to a constant weight at 110° C.

The hardness is calculated as follows:

$$\text{Hardness} = \frac{\text{weight of residue} \times 100}{\text{original weight of carrier (i.e. } 15.0 \pm 0.5 \text{ gm)}}$$

The hardness is therefore a measure of the percent recovery after mixing under the specified conditions.

The bulk density of the carrier according to the present invention is contained by weighing a sample of the carrier to be tested and also determining the volume of this weight. The volume is measured in a measuring cylinder after tapping the measuring cylinder five times from a height of approximately 1 cm.

The specific surface area is that determined on a Strohlein AREA-meter A, model No. B6087-E using nitrogen as the adsorbative.

As stated previously, it has been found that the particulate titanium dioxide preferably should have a purity such that certain impurity levels do not exceed those specifically stated therein. These levels are determined by normal analytical procedures which are readily available.

The invention is described in the following Examples.

EXAMPLE 1

A solution of titanium tetrachloride was prepared by co-adding titanium tetrachloride and water to a flask maintained at a temperature between 0° and 5° C in amounts such that the resultant solution contained the equivalent of 200 gpl $TiO_2$.

Two liters of this titanium tetrachloride solution were heated to the boiling point and to the boiling solution there was added 2 liters of 5 N ammonia solution over a period of one hour while maintaining the solution at the boiling point. A further 400 milliliters of the ammonia solution were then added. The resultant slurry was boiled for 3 hours after which time the precipitated titanium dioxide was allowed to settle whilst the slurry was cooling. The precipitated titanium dioxide was filtered, washed and dried for 48 hours at 110° C.

The titanium dioxide obtained was then heated at 910° C for 3 hours to obtain the carrier in accordance with the present invention.

The carrier was sieved and those particles having a size greater than 500 microns discarded.

The sieved fraction so obtained had a hardness when measured as hereinbefore defined of 96, a bulk density of 1.1 grams per milliliter, and a specific surface area of less than one square meter per gram. The titanium dioxide contained 99.9% by weight of $TiO_2$ in the rutile form.

The carrier was analysed and was found to contain aluminium expressed as $Al_2O_3$ in an amount of less than 0.01%, silicon expressed as $SiO_2$ in an amount of less than 0.01%, phosphorus expressed as $P_2O_5$ in an amount of less than 0.01%, sulphur when expressed as $SO_2$ in an amount of 0.02%, potassium when expressed as $K_2O$ in an amount of 25 parts per million, calcium, zinc, niobium and antimony when expressed with their respective oxides each in an amount of less than 20 parts per million, zinc when expressed as ZnO and lead each in an amount of less than 10 parts per million, chlorine as Cl in an amount of 0.005% by weight and sodium when expressed as $Na_2O$ in an amount of less than 50 parts per million.

A sample of the titanium dioxide carrier obtained was formed into a bed and fluidised with air and heated to 800° C. To this fluidised bed of titanium dioxide there was added finely powdered vanadium pentoxide. The amount of vanadium pentoxide added was such that the catalyst obtained contained 85% by weight $TiO_2$ and 15% by weight $V_2O_5$.

The catalyst so obtained was placed in a tube and heated to 400° C. Through the packed bed within the tube there was passed a mixture of air and o-xylene and the products after passing through the bed collected. The product was found to contain phthalic anhydride. This catalyst had a selectivity of 76% to phthalic anhydride.

A typical commercial catalyst known for use in the oxidation of o-xylene to phthalic anhydride gave 72% selectivity.

A further carrier (as a control) was prepared by taking commercial anatase titanium dioxide prepared by the sulphate process and sieving to obtain a fraction having a particle size within the range 180 to 600 microns. This fraction was treated with vanadium pentoxide by the method described above to obtain an oxidation catalyst. Prior to coating with the vanadium pentoxide, the carrier had a bulk density of 0.7 grams per milliliter, a specific surface area of 9.2 square meters per gram, a hardness of 26 and contained 99.9% $TiO_2$ in the anatase form.

When this catalyst was used in the oxidation of o-xylene to phthalic anhydride it was found to give a selectivity of 73%.

EXAMPLE 2

An anatase titanium dioxide carrier similar to that described in Example 1 was calcined at 945° C for 112 hours. The product was found to have a bulk density of 0.8 grams per milliliter, a specific surface area of less than 2 square meters per gram, a hardness of 63 and contained 1.1% $TiO_2$ in the anatase form.

The carrier so obtained was found to contain impurities within the limits preferred in accordance with this invention and was observed to function as an adequate catalyst carrier for vanadium pentoxide to be used in the oxidation of o-xylene.

EXAMPLE 3

Anatase titanium dioxide prepared by the sulphate process was sieved to produce a desired particle size fraction of size range 210 to 300 microns. 300 grams of this material was placed in a 1200 milliliter polyethylene bottle which was then trundled on a set of laboratory rollers at 90 r.p.m. for 5 hours.

After pelletising the product was heated at 1006° C for 4 hours.

The product obtained was found to have a bulk density of 1.13 grams per milliliter, a specific surface area of 2.2 square meters per gram, a hardness of 76 and contained 99.7% of the $TiO_2$ in the anatase form.

The carrier when treated with vanadium pentoxide was found to be eminently suitable for the oxidation of o-xylene to phthalic anhydride.

EXAMPLES 4 to 14

The procedure of Example 3 was repeated but different samples of the sieved anatase titanium dioxide was trundled at different speeds and the product heated at different temperatures.

The various products obtained were examined and the hardness, rutile content, bulk density and specific surface area determined. The following Table 1 gives details of the calcination temperature and trundling speeds together with results of the physical measurements made on the products.

Table 1

| Example No. | Calcination Temp. °C | Trundling Speed rpm | Hardness | % Rutile | Bulk Density | Specific Surface Area m²/g |
|---|---|---|---|---|---|---|
| 4 | 1100 | 90 | 96 | 89.5 | 1.6 | 0.5 |
| 5 | 1200 | 90 | 98 | 99.6 | 1.6 | 0.5 |
| 6 | 945 | 0 | 63 | 0.1 | 0.8 | 2.2 |
| 7 | 1100 | 0 | 93 | 52.7 | 1.4 | 1.9 |
| 8 | 1100 | 70 | 97 | 89.5 | 1.6 | 0.5 |
| 9 | 1100 | 100 | 100 | 89.5 | 1.6 | 0.5 |
| 10 | 1150 | 0 | 93 | 98.9 | 1.5 | 1.1 |
| 11 | 1150 | 70 | 96 | 99.5 | 1.6 | 0.9 |
| 12 | 1200 | 0 | 95 | 99.9 | 1.6 | 0.8 |
| 13 | 1200 | 70 | 98 | 99.9 | 1.6 | 0.8 |
| 14 | 1200 | 100 | 100 | 99.6 | 1.6 | 0.5 |

EXAMPLE 15

Two liters of 100 gpl aqueous ammonia solution were added to a flask and stirred vigorously. One liter of titanium tetrachloride, diluted with water and containing 200 gpl TiO₂, was added as quickly as possible to the stirring ammonia solution. An immediate precipitate of hydrated titanium dioxide was formed, some of which slowly redissolved on further stirring. Addition of 600 ml of 100 gpl aqueous ammonia solution to the flask precipitated the redissolved titanium dioxide hydrate. Stirring was continued for a further hour, the precipitated titanium dioxide was filtered, washed with two liters of distilled water, reslurried in two liters of distilled water, filtered and washed with a further two liters of distilled water. The precipitate was dried in an oven for 48 hours at 110° C.

The hydrated titanium dioxide so obtained was then calcined at 910° C for 3 hours and washed with two liters of boiling distilled water to produce a catalyst carrier in accordance with the present invention.

What is claimed is:

1. A process for the manufacture of a carrier for an active entity which comprises selecting by sieving from raw anatase titanium dioxide the fraction having a particle size within the range of 150 microns to 350 microns and heating the selected fraction at a temperature of from 850° C. to 1300° C. for a time sufficient to produce a product having a hardness of at least 40, a bulk density of at least 0.8 grams per milliliter and a specific surface area of less than 5 square meters per gram.

2. The process of claim 1 wherein the selected fraction of raw anatase titanium dioxide is pelletized before heating at said temperature of 850° C. to 1300° C.

3. A process for the manufacture of a carrier for an active entity which comprises selecting by sieving from raw granular anatase titanium dioxide having an average particle size of less than 840 microns the fraction having a particle size within the range of 150 microns to 350 microns, and heating the selected fraction at a temperature of from 1050° C. to 1300° C. for a time sufficient to produce a product having a hardness of at least 65, a bulk density of greater than 1.0 grams per milliliter, a specific surface area of less than 3 square meters per gram and with at least 50% by weight of the titanium dioxide in the rutile form.

4. A process for the manufacture of a carrier for an active entity which comprises selecting by sieving from raw granular anatase titanium dioxide having an average particle size of less than 840 microns the fraction having a particle size within the range of 150 microns to 350 microns, pelletizing the selected fraction and heating the pelletized product at a temperature of from 1050° C. to 1300° C. for a time sufficient to produce a product having a hardness of from 85 to 100, a bulk density of from 1.2 to 1.8 grams per milliliter, a specific surface area of from 0.6 to 2 square meters per gram and with at least 50% by weight of the titanium dioxide in the rutile form.

5. A process for the manufacture of a carrier for an active entity comprising precipitating TiO₂ by mixing together in aqueous medium titanium tetrachloride and an alkali, the amounts of alkali and titanium tetrachloride being such that upon completion of the mixing, the mixture has a pH greater than 7, separating the precipitated titanium dioxide, drying the separated titanium dioxide and heating the dried titanium dioxide at a temperature of from 850° C. to 1300° C. for a time sufficient to produce a product having a hardness of from 85 to 100, a bulk density of greater than 1.0 grams per milliliter, a specific surface area of from 0.6 to 2 square meters per gram and with at least 90% by weight of the titanium dioxide in the rutile form.

6. The process of claim 5 wherein an aqueous solution of said alkali is added to an aqueous solution of said titanium tetrachloride.

7. The process of claim 5 wherein an aqueous solution of titanium tetrachloride is added to an aqueous solution of alkali and, after addition of the aqueous titanium tetrachloride solution, additional alkali is added to raise the pH to about 8.

8. A process according to claim 5 in which said bulk density is from 1.2 to 1.8 grams per milliliter.

9. A process according to claim 1 in which said product is then coated with vanadium pentoxide.

10. A process according to claim 5 in which said product is then coated with vanadium pentoxide.

11. A process for the manufacture of a carrier for an active entity which comprises selecting by sieving from raw anatase titanium dioxide the fraction having a particle size within the range 150 microns to 350 microns and heating the selected fraction at a temperature and for a time sufficient to produce a product having a hardness of at least 40, a bulk density of at least 0.8 grams per milliliter, a specific surface area of less than 5 square meters per gram and with at least 90% by weight of the titanium dioxide in the rutile form.

* * * * *